| United States Patent [19] | [11] Patent Number: 4,737,318 |
|---|---|
| Ichino et al. | [45] Date of Patent: Apr. 12, 1988 |

[54] RECOVERY OF ACETIC ANHYDRIDE

[75] Inventors: Masaaki Ichino; Kunio Koga; Tsutomu Mizuta; Takashi Matsuyama, all of Himeji, Japan

[73] Assignee: Daicel Chemical Industries, Ltd., Osaka, Japan

[21] Appl. No.: 910,335

[22] Filed: Sep. 19, 1986

Related U.S. Application Data

[63] Continuation of Ser. No. 717,626, Mar. 29, 1985.

[30] Foreign Application Priority Data

Mar. 30, 1984 [JP] Japan ................... 59-62660

[51] Int. Cl.$^4$ ............................................. C07C 51/54
[52] U.S. Cl. ................................................... 260/547
[58] Field of Search ........................................ 260/547

[56] References Cited

U.S. PATENT DOCUMENTS

| 1,815,802 | 7/1931 | Schleicher et al. | 260/547 |
| 1,915,573 | 6/1933 | Green et al. | 260/547 |
| 1,996,755 | 4/1935 | Dreyfus | 260/547 |
| 2,160,842 | 6/1939 | Dreyfus | 260/547 |
| 2,872,481 | 2/1959 | Vogt | 260/547 |

Primary Examiner—Paul J. Killos
Attorney, Agent, or Firm—Flynn, Thiel, Boutell & Tanis

[57] ABSTRACT

Acetic anhydride is recovered from a mixture of acetic anhydride, acetic acid and water by contacting the mixture with at least one extraction solvent selected from the group consisting of a hydrophobic, organic solvent, a ketone and an ester to extract and recover acetic anhydride.

5 Claims, 1 Drawing Sheet

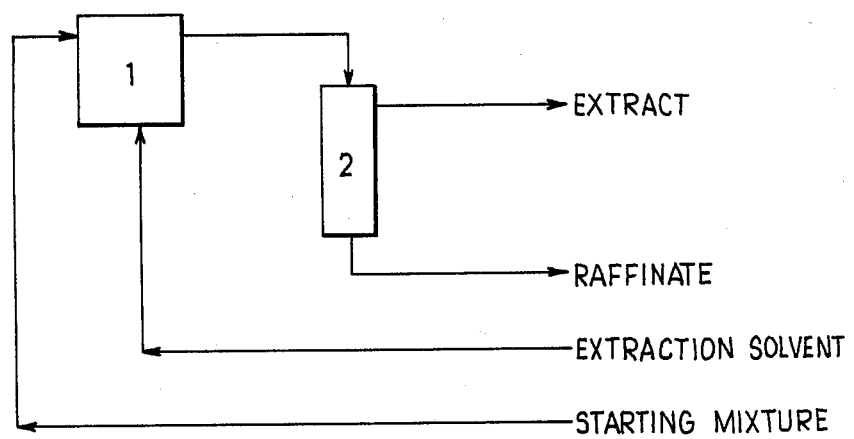

RECOVERY OF ACETIC ANHYDRIDE

This application is a continuation of U.S. Ser. No. 717,626, filed Mar. 29, 1985.

The present invention relates to a process for recovering acetic anhydride from an aqueous solution containing acetic anhydride and acetic acid.

More particularly, the present invention relates to a process for recovering acetic anhydride from an aqueous solution containing acetic anhydride and acetic acid, which comprises a condensate obtained in a step of cooling a decomposition gas formed in the production of ketone by pyrolyzing acetic acid and cooling the formed gas.

A well-known industrial production process of ketene consists in continuously pyrolyzing acetic acid at 700° C. or above in the presence of a catalyst. In order to obtain ketene by purification of the pyrolysis gas, it is necessary to separate a condensible gas. For this purpose, it is necessary to cool the pyrolysis gas as rapidly as possible, and the ketene gas is recovered by separating the condensible component from the pyrolysis gas by cooling. At this time, both acetic anhydride and acetic acid are formed inevitably in the condensed component by contact among part of the formed ketene, unpyrolyzed acetic acid, and the formed water. Therefore, a condensate comprising water, acetic acid and acetic anhydride should be obtained in the cooling step. However, because of the presence of water in the condensate, the acetic anhydride is hydrolyzed into acetic acid with the lapse of time. Since this is a great loss in a process in which acetic anhydride is produced from the purified ketene, it is preferable that the acetic anhydride be recovered from said condensate before it is hydrolyzed.

As a result of an investigation about the recovery and use of acetic anhydride from said condensate, which has heretofore not been performed, the inventor of the present invention has found a solvent which not only has a high distribution coefficient, a high selectivity and a low mutual solubility in water but also allows easy purification of extracted acetic anhydride, and achieved the present invention.

Namely, it is an object of the present invention to provide a process for recovering acetic anhydride, characterized by contacting an aqueous solution containing acetic anhydride and acetic acid with at least one solvent selected from the group consisting of hydrophobic organic solvents, ketones, and esters to thereby extract and recover the acetic anhydride. According to the process of the present invention, it is possible to recover to industrial advantage acetic anhydride which has heretofore been lost.

The solvent used in the present invention comprises at least one member selected from the group consisting of hydrophobic organic solvents such as aliphatic hydrocarbons, alicyclic hydrocarbons and aromatic hydrocarbons, each having a boiling point of from 0° to 250° C., ketones, esters, and mixtures thereof. Examples of the solvents include heptane, nonane, cyclopentane, cyclohexane, methylcyclohexane, benzene, ethylbenzene, xylene, methyl isobutyl ketone, and ethyl acetate.

When these hydrophobic organic solvents, ketones or esters are used, the following advantages can be obtained:

(1) these solvents can extract acetic anhydride selectively from an aqueous solution containing acetic anhydride and acetic acid, (2) when the above hydrophobic organic solvents are used for extracting said aqueous solution, the distribution coefficients for acetic anhydride are high, and the amount of acetic acid lost by hydrolysis is very small since the amount of entrained water is very small, and (3) when the hydrophobic organic solvents as mentioned above are used, the amount of the water entrained with an extract is very small, so that it is possible to reduce the hydrolysis of acetic anhydride in a rectification step to a very small extent.

Although well-known, ordinary batchwise or continuous extractors can be used in the present invention, those which can permit rapid and efficient contact of an aqueous solution containing acetic anhydride and acetic acid with the above-described solvents such as hydrophobic organic solvents, ketones, or esters are desirable and, for example, a mixer-settler type of an agitating extractor, a tower extractor, etc., can be used suitably. With respect to the operating conditions, the solvent to feed ratio is from 0.1 to 2.0, preferably from 0.2 to 1.5 (by weight). When this ratio is lower than 0.1, the amount of acetic anhydride extracted is decreased, while when it exceeds 2.0, the amount of the solvent used is increased, though the amount of acetic anhydride extracted is increased, which is not desirable. An extraction temperature practically ranges from 0° C. to 60° C., preferably 10° C. to 60° C., more preferably from 20° C. to 50° C. A temperature lower than 0° C. will not be economical because of excessive cooling. The range of 10° C. to 60° C. is preferably set because the distribution coefficient for acetic anhydride may increase and therefore the amount of acetic acid extracted may also increase. When the temperature exceeds 60° C., the hydrolysis of acetic anhydride increases, which is not desirable.

Although the acetic anhydride extracted with the above-described solvents, such as hydrophobic organic solvents, ketones, or esters, can be used as such, it is preferable that it is isolated by distillation. Any of commonly used distillation apparatus may serve this purpose.

BRIEF DESCRIPTION OF THE DRAWING

The drawing is a flow diagram of the extraction process in Example 2.

The present invention provides a process especially useful for selectively recovering acetic anhydride from a condensate formed in the step of cooling the pyrolysis gas produced in a process for producing acetic anhydride by purifying ketene formed by pyrolysis of acetic acid.

The present invention will now be described in detail with reference to examples.

EXAMPLE 1

The extraction of acetic anhydride was carried out by using each of four kinds of solvents: benzene, xylene, methyl isobutyl ketone, and ethyl acetate. The feed had a composition of 15 wt. % of acetic anhydride, 35 wt. % of acetic acid, and 50 wt. % of water. The extraction procedure consisted of placing 40 g of the feed and 40 g of a solvent in a 100-ml separatory funnel and agitating the mixture well for 30 seconds. The mixture was separated into an extract and a raffinate, and each sample was analyzed quantitatively for its components. The extraction temperature was 25° C. Table 1 shows the distribution coefficients for acetic anhydride, acetic acid and water between an extract and a raffinate.

TABLE 1

Distribution coefficients ($m_i$) for acetic anhydride, acetic acid and water

| Solvent *Distribution coefficient | Benzene | Xylene | Methyl isobutyl ketone | Ethyl acetate |
| --- | --- | --- | --- | --- |
| $m_1$ (acetic anhydride) | 1.2~1.3 | 0.70 | 0.40 | 2.40 |
| $m_2$ (acetic acid) | 0.17~0.20 | 0.11 | 0.91 | 1.80 |
| $m_3$ (water) | 0.005 | 0.002 | 0.13 | 0.084 |

Note *1 distribution coefficient ($m_i$) = $\dfrac{\text{component i in extract (wt. \%)}}{\text{component i in raffinate (wt. \%)}}$ i: 1 = acetic anhydride, 2 = acetic acid, 3 = water.

EXAMPLE 2

A solution of 15 wt. % of acetic anhydride, 35 wt. % of acetic acid and 50 wt. % of water was used as a feed, and the selective recovery of acetic anhydride was carried out by using benzene as a solvent under a condition of a solvent to feed ratio of 0.5 (by weight) and an extraction temperature of 40° C. by means of a mixer-settler type agitating extractor. The feed rate was 1,000 to 2,000 grams per hour and a residence time in the mixer was 1~3 minutes. The drawing shows the flow sheet in this example. The drawing, 1 is a mixer and 2 is a settler. It was found that the composition of the extract was 20.2 wt. % of acetic anhydride, 8.4 wt. % of acetic acid, 0.5 wt. % of water, and 70.9 wt. % of benzene, the composition of the raffinate was 3.4 wt. % of acetic anhydride, 42.5 wt. % of acetic acid, 0.3 wt. % benzene, and 53.8 wt. % of water, the rate of recovery of acetic anhydride was 80 wt. %, and the rate of hydrolysis of acetic anhydride was 3.0%.

EXAMPLE 3

Extraction of acetic anhydride was conducted in the same way as shown in Example 1, except for using benzene and ethyl acetate as a solvent for extraction and an extraction temperature of 30° C. Results are shown in Table 2.

TABLE 2

| Distribution coefficient | Solvent | |
| --- | --- | --- |
| | Benzene | Ethyl acetate |
| $m_1$ (acetic anhydride) | 2-5 | 2-5 |
| $m_2$ (acetic acid) | 0.1-0.5 | 1-5 |
| $m_3$ (water) | 0.001-0.02 | 0.05-0.1 |

EXAMPLE 4

Selective recovery of acetic anhydride was effected in the same manner as in Example 2, except for an extraction temperature of 30° C. and a feed rate of 2000 g/h. As a result it was found that the composition of the extract was 18.5 wt.% of acetic anhydride, 7.4 wt.% of acetic acid, 0.4 wt.% of water, and 73.7 wt.% of benzene, and then the composition of the raffinate was 2.5 wt.% of acetic anhydride, 37.0 wt.% of acetic acid, 60.2 wt.% of benzene and 0.3 wt.% of water. A recovery rate of acetic anhydride was 83 wt.% and a hydrolysis rate of acetic anhydride was 2.7 wt.%.

The embodiments of the invention in which an exclusive property or privilege is claimed are defined as follows:

1. In a process for preparing ketene which comprises pyrolyzing acetic acid to obtain a vapor-phase pyrolysis product containing ketene, acetic anhydride, water and unreacted acetic acid, then rapidly cooling said vapor-phase pyrolysis product to separate ketene from a condensate which is an aqueous solution of acetic anhydride and acetic acid, the improvement which comprises: mixing said condensate with from 0.1 to 2.0 times by weight, based on the weight of said condensate, of at least one extraction solvent selected from the group consisting of hydrophobic hydrocarbon solvents, ketones and esters, under liquid-liquid extraction conditions, at an extraction temperature of 0° to 60° C., and thereby preferentially extracting acetic anhydride into said extraction solvent and separately recovering an extract phase enriched with acetic anhydride and a raffinate enriched with acetic acid and water.

2. A process as claimed in claim 1, in which said hydrophobic organic solvent is an aliphatic hydrocarbon, an alicyclic hydrocarbon or an aromatic hydrocarbon, each having a boiling point of 0° C. to 250° C.

3. A process as claimed in claim 1, in which said extraction solvent is selected from the group consisting of heptane, nonane, cyclopentane, cyclohexane, methylcyclohexane, benzene, ethylbenzene, xylene, methyl isobutyl ketone and ethyl acetate.

4. A process as claimed in claim 1, in which said extraction temperature is in the range from 20°-50° C.

5. A process as claimed in claim 1, in which said extraction solvent is selected from the group consisting of benzene, xylene, methyl isobutyl ketone and ethyl acetate.

* * * * *